United States Patent [19]

Leighton et al.

[11] 4,308,351

[45] Dec. 29, 1981

[54] SYSTEM FOR GROWING TISSUE CULTURES

[76] Inventors: Joseph Leighton, 1201 Waverly Rd., Gladwyne, Pa. 19035; David E. Butz, 1 Indian Run Trail, Littleton, Mass. 01460

[21] Appl. No.: 141,395

[22] Filed: Apr. 18, 1980

[51] Int. Cl.$^3$ .............................................. C12M 3/00
[52] U.S. Cl. .................................... 435/284; 435/240; 435/241; 435/285; 435/286
[58] Field of Search ................ 435/284, 285, 286, 240, 435/241, 297, 298, 299, 300, 301

[56] References Cited

U.S. PATENT DOCUMENTS

| | | | |
|---|---|---|---|
| 2,942,520 | 6/1960 | Rose | 435/284 X |
| 3,065,669 | 11/1962 | Orsi | 435/284 X |
| 3,275,528 | 9/1966 | Ainis | 435/284 X |
| 3,503,665 | 3/1970 | Carter | 435/284 X |
| 3,726,767 | 4/1973 | White | 435/285 |
| 3,745,091 | 7/1973 | McCormick | 435/285 |
| 4,060,457 | 11/1977 | Iizuka et al. | 435/284 |
| 4,073,695 | 2/1978 | Lyman | 435/284 |

OTHER PUBLICATIONS

J. Leighton et al., Abstract presented at National Bladder Cancer Project Investigators' Workshop; Dec. 1978.
Joseph Leighton, Histophysiologic Gradient Culture, Laboratory Investigation, vol. 40, No. 2, p. 1; 1979.
Joseph Leighton et al., Histophysiologic Diffusion Gradient Culture, In Vitro, vol. 15, p. 174; 1979.
Joseph Leighton, Histophysiologic Gradient Culture, Delivered to American Cancer Society Science Writers Seminar; Mar. 1979.
Joseph Leighton et al., Histophysiologic Gradient Culture of Stratified Epithelium, Presented at International Conference on Methods to Culture Normal Human Tissues & Cells at NIH; 1979.
Paul F. Krase, Jr. et al., Editors, Tissue Culture Methods and Applications, pp. 367–371, Academic Press; 1973.

*Primary Examiner*—Robert J. Warden
*Attorney, Agent, or Firm*—Wolf, Greenfield & Sacks

[57] ABSTRACT

An apparatus for growing tissue cultures in vitro in which the process of growth occurring in nature is more nearly simulated. The apparatus permits a concentration gradient of nutrients to develop through a permeable membrane to which a sample of tissue is attached. The apparatus is such that the growing culture receives substantially all its nutrients and oxygen necessary for growth through the membrane.

The permeable membrane is attached to one side of a support and covers one end of a well in the support. A tissue sample is placed within the well and attached to the inside surface of the permeable membrane. A specially designed closed container filled with solution encases the membrane, support, and tissue sample. The container and contents are submerged in a nutrient bath. A concentration gradient develops in the tissue culture as nutrients and oxygen permeate through the membrane to the tissue sample. At least one culture container, and preferably two culture containers, are integral with a plastic plate which has dimensions comparable to a standard microscope slide. The state of growth occurring within the culture containers may be viewed periodically with an inverted microscope without opening the container.

The invention has particular application in the field of cancer research in the study of the development of cancerous tissue and has potential for pathological diagnosis of the malignant character of tissue cells.

12 Claims, 7 Drawing Figures

U.S. Patent   Dec. 29, 1981   4,308,351
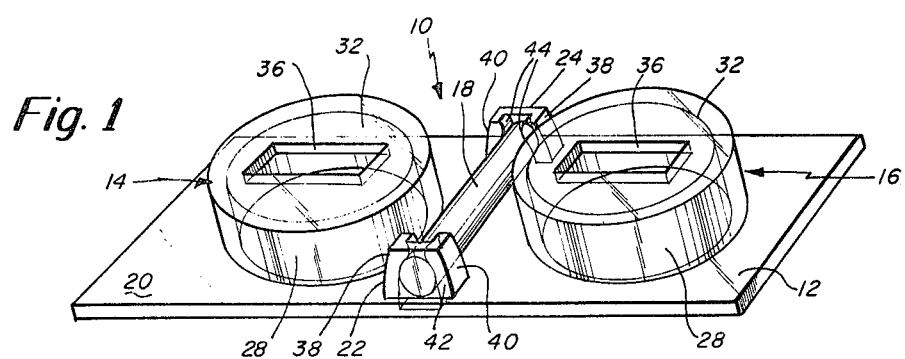
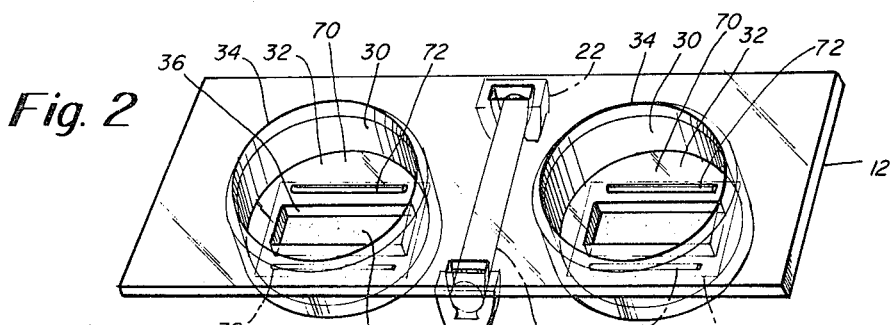
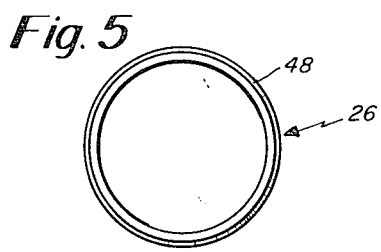
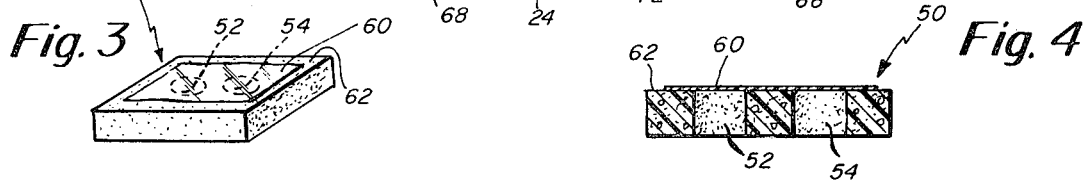
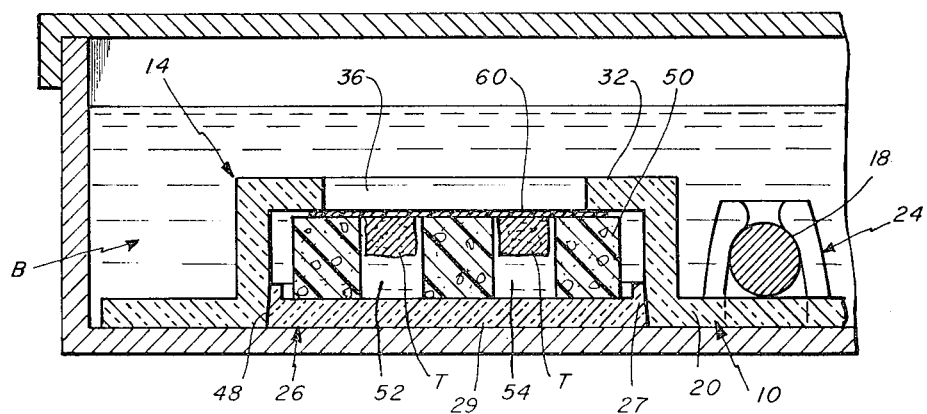

SYSTEM FOR GROWING TISSUE CULTURES

BACKGROUND OF THE INVENTION

This invention relates to a system for growing tissue cultures and more particularly comprises a new and improved culture chamber and tissue support that provide for the supply of nutrients and oxygen to tissue samples under spatial conditions simulating those that occur in nature.

In the conventional art of in-vitro growth of mammalian tissues, tissue samples are affixed to the bottom of a tube or petri dish and bathed from above with a nutrient solution. In this conventional mode the tissue culture receives nutrients from above, i.e., from the side opposite the side attached to the tube or petri dish. This arrangement is contrary to the situation in the body where the plane of attachment of epithelial tissue to the underlying connective tissue is also the path of nutrient exchange. This conventional prior art method makes the diagnosis and prediction of the malignant character of many epithelial tissue disorders very difficult.

SUMMARY OF THE INVENTION

Use of the apparatus of the present invention simulates more nearly the growth process occurring naturally in living species by providing means whereby the nutrients and oxygen pass to the growing culture from the side of attachment of the tissue to its support. Thus, use of the apparatus of the present invention, by more nearly simulating the process and conditions through which mammalian tissue growth occurs in nature, may make much easier the diagnosis and prediction of tissue disorders. The method practiced with the present invention more nearly reproduces the spatial organization found in nature with a nutrient diffusion gradient delineating the structure of tissue, such as a stratified epithelium, into a deep zone of growth, an intermediate zone of maturing cells, and a superficial zone of fully matured cells. The present invention, therefore, has far reaching implications in the fields of developmental biology, pathology, and cancer research. For example, tissue grown in the apparatus of the present invention, with sample tissue taken from an organ of a patient such as the bladder or cervix may enable the pathologist to diagnose more accurately the malignant character of many disorders of epithelial tissues.

One important object of the present invention is to provide an apparatus for the growth of tissue in vitro, which apparatus enables the user more nearly to simulate the natural process of tissue growth in vivo, so as to provide a particularly useful tool in the field of surgical pathology for the study of the development and diagnosis of cancerous tissue.

A more specific object of the present invention is to provide an apparatus which develops a more natural histophysiological gradient for the supply of nutrients and oxygen to a tissue sample.

Another object of the present invention is to provide a membrane support which is soft enough to be cut with a microtome blade when sections of the tissue culture are taken for microscopic analysis.

It is a further object to provide an enclosed container for the membrane with its support and the tissue sample, whereby the membrane side opposite to which the sample is attached is exposed to an external supply of nutrients while the side of the membrane to which the sample is attached confronts a transparent wall of the container. Periodic microscopic examination of the state of culture growth may be made through the transparent wall.

In accordance with this invention a tissue sample is attached to one side of a membrane that may, for example, be a collagen material. Alternatively the membrane may be any other suitable hydrated gel. The membrane must be of a material that allows the passage of nutrients and oxygen through it, that is structurally sound so as to withstand agitation and heat, and that does not dissolve in the solution. The cells must readily attach to it. The permeable membrane is attached to one side of a membrane support that has at least one well in which the tissue sample lies secured to the membrane. A support composed of a fine pore synthetic cellulose sponge material is particularly suitable. The support-permeable membrane-tissue sample assembly is placed within the culture container of the invention. The container, placed in a laboratory culture vessel, is bathed in a nutrient solution for a period of time sufficient to permit significant culture growth to occur.

The culture container of the invention is specially designed to permit a nutrient concentration gradient to occur in the tissue as a result of nutrients and oxygen diffusing through the permeable membrane to the tissue sample. This permits the tissue culture to receive substantially all the supply of nutrients and oxygen from the side attached to the permeable membrane.

The culture container of the invention is an integral part of a transparent plate preferentially having overall dimensions similar to that of a standard microscope slide. The gradient culture plate also includes a ballast pin to sink the plate in the bath.

In the preferred embodiment of the invention the culture container is comprised of a shallow cylinder which is open at one end and closed at the other. The closed end of the container has an aperture sufficiently large so that the wells in the membrane support are exposed through it when the support is placed in the container. The open end of the container, through which it is loaded, is closed by a circular cover.

BRIEF FIGURE DESCRIPTION

FIG. 1 is an isometric view of the preferred embodiment of the gradient culture plate of this invention, in its operative position.

FIG. 2 is an isometric view of the gradient culture plate shown in FIG. 1, but in position for loading and with the container covers removed.

FIG. 3 is an isometric drawing of one permeable membrane with its support, which is used with the culture plate illustrated in FIGS. 1 and 2.

FIG. 4 is a cross sectional view of the membrane and support shown in FIG. 3.

FIG. 5 is a plan view of one container cover which is used to seal the open end of one culture container of the culture plate shown in FIGS. 1 and 2.

FIG. 6 is a cross sectional view of the cover shown in FIG. 5.

FIG. 7 is a fragmentary cross sectional view of the tissue culture plate shown immersed in a nutrient bath and containing a membrane and support in its container, and with the membrane carrying tissue samples, in accordance with this invention.

DETAILED DESCRIPTION

The gradient culture plate 10 shown in FIGS. 1 and 2 includes a base plate 12, a pair of containers 14 and 16, and a ballast pin 18 retained on the upper surface 20 of base plate 12 by clips 22 and 24. As viewed in the operative position of FIG. 1, the containers are open at the bottom and substantially closed at the top. The open end of each container may be closed by a bottom cover 26 such as shown in FIGS. 5 and 6. The base plate 12 with containers 14 and 16 and clips 22 and 24 is preferably made as a unitary structure from transparent plastic material. The embodiment shown is injection molded of clear polystyrene, but it may be vaccum formed from thin sheet material.

Base plate 12 preferably is of standard microscope slide dimensions, i.e. approximately 2.5×7.5 cm (1×3 inches) so that it may be used with a conventional inverted microscope. Identical containers 14 and 16 are each defined by a cylindrical wall 28 that forms a shallow chamber or well 30 partially closed at the top by top wall 32. The bottom is open as shown in FIG. 2 through holes 34 in the base plate 12. The top wall 32 of each container has a rectangular aperture 36 for purposes which will be made apparent presently. For maximum capacity, the diameter of each cylindrical container approximates the width of the base plate 10 as is evident in FIG. 1.

The ballast pin 18, which typically may be made of stainless steel or some other suitable non-corrosive material, is mounted along the center line of the base plate 12 by means of clips 22 and 24. The clips are generally U-shaped in plan and face one another across the center of the plate. Each clip includes opposite side walls 38 and 40 and an end wall 42. Beads 44 are formed along the upper edge of the inner surface of each side wall 38 and 40, as viewed in FIG. 1, so as to enable the ballast pin to be removably snapped into place. The space between the facing beads 44 is very slightly smaller than the diameter of the ballast pin 18 so that the pin may be snapped by the beads into the operative position.

As indicated above, access to the interior of the containers is provided through the open bottom ends. A stopper-like bottom cover 26, suitable for sealing each container, is shown in FIGS. 5 and 6. The bottom cover 26 preferably is thickened at its rim 27 and the thickness of its thinner central portion 29 is equal to that of the plate 12. The cover is made of a clear plastic material such as polystyrene. Its side edges 48 may be slightly tapered, at perhaps 2°, to facilitate insertion of the cover into the holes 34. The holes 34 may be provided with a similar taper to assist in the formation of a seal.

In FIGS. 3 and 4 a culture support 50 to be used in the containers 14 and 16 is shown. In the preferred form, the support is made of an inert, lightweight material, such as a fine pore synthetic cellulose sponge, and may be approximately 10×15 mm. in plan and 4 mm in thickness so that it readily fits within the containers 14 and 16. Two wells 52 and 54 extend through the support 50, and each may be approximately 6 mm in diameter and spaced approximately 1 mm apart. A thin membrane 60, preferably formed of a collagen dispersion such as that manufactured by Ethicon, Inc., of Sommerville, N.J., is secured to the upper surface 62 of the sponge support. The membrane may have a thickness of approximately 15 microns. While a particular collagen dispersion is suggested, it will be appreciated that the membrane may be made of other materials as well. For example, hydrated gels such as N-vinyl pyrrolidone may also be used. The membrane must allow the passage of nutrients and oxygen, and must be structurally capable of withstanding agitation and heat. It, of course, must not be soluble in solution.

In use, the tissue samples T to be studied are placed in the wells 52 and 54 of the support 50 and affixed to the inner surface of the membrane 60. The plate 10 is inverted to the position shown in FIG. 2 and the bottom covers 26 are removed to provide access to the interior of the containers. An adhesive strip 68 or some similar closure may be provided over each of the apertures 36 on the outer surface of the top walls 32 of the containers to prevent any solution within the containers from dripping out. An assembly composed of the tissue sample, membrane, and support is placed in each container resting on the inner surface 70 of top wall 32 with the wells 52 and 54 aligned with the closed aperture 36, and the wells are filled with solution. The covers 26 are then applied to the containers. Preferably the lower surface 70 of each top wall 32 is provided with a pair of ribs 72 along the sides of the apertures 36 so as to retain the support 50 in alignment with the aperture. The strips 68 will retain the solution in the containers.

The culture plate is then reinverted to the position of FIG. 1. The strips 68 are removed, and the plate is placed in a nutrient bath B as suggested in FIG. 7. The ballast pin 18 will cause the plate to sink to the bottom of the laboratory vessel. The tissue sample T attached to the membrane in each container receives oxygen and nutrients by diffusion through the membrane from the nutrient bath as the membrane is exposed to the bath through the apertures 36. Because each container is sealed, the only access for the nutrient solution to the tissue cultures is through the apertures and membrane. The nutrient solution must be of sufficient quantity so that it just covers the whole apparatus.

From time to time the tissue culture may be examined with an inverted microscope without removing the tissue sample or its support 50 from the plate, or the plate from the laboratory vessel. The transparent bottom covers 26 allow the cultures to the examined without their removal. After significant growth of the culture has occurred, the support 50 may be removed from its container and the culture may be sectioned with a conventional microtome. Because the support 50 is made of a fine pore synthetic cellulose sponge material, or some other similar material having like characteristics, the sections may be cut readily with a microtome.

Having described this invention in detail, those skilled in the art will appreciate that numerous modifications may be made thereof without departing from the spirit of the invention. For example, the plate and covers could well be vacuum formed rather than molded as suggested by the structure of the embodiment shown, and a variety of materials may be used. The covers, of course, could be other than stopper-like, and the strips used to cover each aperture could have other configurations. Therefore, it is not intended that the scope of this invention be limited to the specific embodiment illustrated and described. Rather, its scope is to be determined by the appended claims and their equivalents.

What is claimed is:
1. Apparatus for growing tissue in vitro comprising:
   a support having an internal wall surface defining a well extending therethrough;

a permeable membrane attached to one side of the support and covering one end of the well, said membrane being capable of carrying a tissue sample attached to the side of the membrane facing the well;

and means for establishing a concentration gradient through the membrane so that the tissue culture receives substantially all of its supply of nutrients and oxygen from the side of the tissue sample attached to the membrane; said means including a container adapted to receive the support with the attached membrane and tissue sample; said container having an aperture sufficiently large so that when the support is placed within the container the membrane is exposed to the external environment through said aperture, the nutrient concentration gradient being established through the membrane surface exposed through said aperture when the container is immersed in an external bath of nutrient solution to begin the growth process.

2. Apparatus as defined in claim 1 further characterized by:

the support having at least two wells therein.

3. A culture plate for growing tissue in vitro comprising:

a base plate;

at least one culture container affixed to the base plate, said culture container having an upstanding wall emanating from the base plate;

an opening in one end of said container through which a tissue sample may be introduced;

a removable cover for closing said opening to seal said one end;

a wall closing the other end of the container for carrying a culture support, and an aperture provided in the said wall closing the other end of the container for the entry of nutrients and oxygen to the container interior.

4. A culture plate as defined in claim 3 further characterized by:

a ballast pin attached to the base plate for sinking it in a nutrient solution.

5. A culture plate as defined in claim 4 further characterized by:

a pair of clips attached to the base plate approximately along the center line of the culture plate, said clips releasably retaining the ballast pin on the base plate.

6. An assembly for growing tissue comprising:

a flat plate approximately the size of a standard microscope slide;

at least one cylindrical container formed as an integral part of the plate on one surface thereof, with an opening through the plate providing access to the container through one end thereof;

a removable end wall closing one end of the container and a fixed wall particularly closing the other end of the container;

an aperture in the fixed wall through which a nutrient solution may pass to the interior of the container;

a cellulose support having a well therein and adapted to be mounted in the container with the well aligned with the aperture;

a permeable membrane attached to the support and closing one end of the well, said membrane lying across the aperture when the support is disposed in the container, said membrane being capable of carrying a tissue sample on its surface facing the well;

and a ballast member attached to the plate for submerging the plate with its container in a nutrient bath.

7. An assembly for growing tissue as defined in claim 6 further characterized by:

said plate carrying a second container identical to the first described container for receiving a second support.

8. An assembly for growing tissue as defined in claim 7 further characterized by:

each support having two wells covered by the membrane, each well receiving a tissue sample.

9. In an assembly for growing tissue in vitro wherein the tissue sample is carried on a membrane which in turn is carried by a support; a container adapted to be immersed in a nutrient bath, said container comprising a side wall and two end walls, one of said end walls being removable enabling the support to be placed within the container, one of said end walls also having a surface for engaging the surface of the membrane opposite the membrane surface carrying the tissue sample when the support is in the container, and an aperture in the end wall having said surface and adapted to be closed by the membrane so that nutrients and oxygen can reach the tissue sample through the membrane when the container is immersed in the nutrient bath.

10. In an assembly for growing tissue in vitro as defined in claim 9, the improvement comprising the removable end wall and the end wall having the surface engaging the membrane being the opposite walls.

11. In an assembly for growing tissue in vitro as defined in claim 9, the improvement comprising said support being made of a cellulose material capable of being sectioned by a microtome blade;

and a well in the support for housing the tissue sample when the sample is carried by the membrane.

12. In an assembly for growing tissue in vitro as defined in claim 9, the improvement comprising said container being made of transparent material enabling a tissue culture to be examined without removal thereof from the container.

* * * * *